United States Patent [19]
McGeer et al.

[11] Patent Number: 5,776,946
[45] Date of Patent: Jul. 7, 1998

[54] PERIPHERAL BENZODIAZEPINE RECEPTOR LIGANDS AS ANTIINFLAMMATORY AGENTS

[76] Inventors: Patrick L. McGeer; J. Douglas Waterfield; Edith G. McGeer, all of Kinsmen Laboratory of Neurological Research, The University of British Columbia, 2255 Wesbrook Mall, Vancouver, British Columbia, Canada, V6T 1Z3

[21] Appl. No.: 520,211

[22] Filed: Aug. 28, 1995

[51] Int. Cl.$^6$ .................................................. A61K 31/47
[52] U.S. Cl. .................................... 514/307; 514/221
[58] Field of Search ................................ 514/221, 307

[56] References Cited

U.S. PATENT DOCUMENTS

| | | | |
|---|---|---|---|
| 4,788,199 | 11/1988 | Benvides et al. | 514/259 |
| 4,788,204 | 11/1988 | Benavides et al. | 514/311 |
| 4,808,599 | 2/1989 | Dubroeucq et al. | 514/320 |
| 5,185,442 | 2/1993 | Weber et al. | 514/14 |
| 5,192,753 | 3/1993 | McGeer et al. | 514/311 |
| 5,488,064 | 1/1996 | Sher | 514/465 |
| 5,550,124 | 8/1996 | Gee | 514/221 |

FOREIGN PATENT DOCUMENTS

WO93/1177  6/1993  WIPO.

OTHER PUBLICATIONS

Bartlett et al., Development of Autoimmunity in MRL/lpr Mice and the Effects of Drugs on this Murine Disease, Scand J Rheumatol—Suppl 1988; 75:290–299.
Bessler et al., Immunomodulatory Effect of Peripheral Benzodiazepine Receptor Ligands on Human Mononuclear Cells, J Neurimmunol 1992; 38: 19–26.
Diorio et al., Peripheral Benzodiazepine Binding Sites in Alzheimer's Disease Frontal and Temporal Cortex, Neurobiol Aging 1991; 12: 255–258.
Doble et al., Labelling of Peripheral–type Benzodiazepine Binding Sites in Human Brain with [3H] PK 11195: Anatomical and Subcellular Distribution, Brain Res Bull 1987; 18; 49–61.
Hayashi et al., Pathogenesis of Sjorgren's Syndrome–Like Autoimmune Lesions in MRL/lpr Mice [Review], Pathol Int. 1994; 44:559–568.
Hirsch et al., Characterization of Ligand Binding to Mitochodrial Benzodiazepine Receptors, Mol Pharmacol 1989; 35: 164–172.
Junck et al., PET Imaging of Human Gliomas with Ligands for the Peripheral Benzodiazepine Binding Site, Ann Neurol 1989; 26 752–758.
Klegeris et al., Inhibiton of Respiratory Burst in Macrophages by Complement Receptor Blockade, Eur J Pharmacol 1994; 260: 273–277.
Koopman et al., The MRL–lpr Mouse. A Model for the Study of Rheumatoid Arthritis [Review], Scand J Rheumatol—Supp 1988; 75: 284–289.

Lenfant et al., In vivo Immunomodulating Activity of PK 11195, a Structurally Unrelated Ligand for Peripheral Benzodiazepine Binding Sites. I. Potentiation in Mice of the Humoral Response to Sheep Red Blood Cells, Int. J. Immunopharmacol 1986; 8, 825–828.
Leong et al., Increased Densities of Binding Sites for the "Peripheral–type" Benzodiazepine Receptor Ligand [3H] PK11195 in Vulnerable Regions of the Rat Brain in Thiamine Deficient Encephalopathy, J Cereb Blood Flow Metab 1994; 14: 100–105.
McGeer et al., Peripheral–type Benzodiazepine Binding in Alzeheimer Disease, Alz Dix Assoc Disorders 1988; 2: 331–336.
Myers et al., Macrophage and Astrocyte Populations in Relation to [3H]PK 11195 Binding in Rat Cerebral Cortex Following a Local Ischaemic Lesion, J. Cerebral Blood Flow Metab 1991; 11: 314–322.
Ramsier et al., In vitro Inhibition of Cellular Immune Responses by Benzodiazepines and PK 11195, Immunopharmacol Immunotoxicol 1993; 15: 557–582.
Ratkay et al., Photodynamic Therapy: a Comparison with other Immunomodulatory Treatments of Adjuvant–enhanced Arthritis in MRL–lpr Mice, Clin Exp Immunol 1994; 95: 373–77.
Ratkay et al., Complete Freund's Adjuvant Induces an Earlier and More Severe Arthritis in MRL–lpr Mice, J Immunol 1993; 151:5081–5087.
Rosenberg, Neuromuscular Histopathology in (New Zealand Black × New Zealand White) F1 and MRL–lpr Autoimmune Mice: Models for Skeletal Muscle Involvement in Connective Tissue, Disease, Arthritis Rheumatism 1988; 31: 806–811.
Sakic et al., Brain–Reactive Antibodies and Behavior of Autoimmune MRL–lpr Mice, Physiol Behavior 1993; 54: 1025–1029.
Schoemaker et al., Specific High Affinity Binding Sites for [$^3$H]Ro 5–4864 in Rat Brain and Kydney, J Pharm Exp Ther 1983; 225: 61–69.
Synder et al., Molecular Mechanism of Peripheral Benzodiazepine Recepators, Neurchem Res 1990; 15: 1992–123.
Vogelweid et al., Inflammatory Central Nervous System Disease in Lups–prone MRL/lpr Mice: Comparative histologic and Immunohistochemical findings, J Neuroimmunology 1991; 35; 89–99.

(List continued on next page.)

Primary Examiner—James H. Reamer
Attorney, Agent, or Firm—Oyen Wiggs Green & Mutala

[57] ABSTRACT

Compounds which bind with high affinity to peripheral benzodiazepine receptors are useful as antiinflammatory agents. Such compounds include isoquinoline and benzodiazepine derivatives, such as PK 11195. A method of treating an inflammatory condition in a mammal with such compounds is provided. Pharmaceutical compositions comprising such compounds are provided. A method is provided for identifying compounds that are therapeutically effective for treating inflammatory conditions.

14 Claims, No Drawings

OTHER PUBLICATIONS

Zavala et al., *Interaction of Benzodiazepines with Mouse Macrophages*, Eur J Pharmac 1984; 106: 561–566.

Zavala et al., *Peripheral Benzodiazepines Enhance the Respiratory Burst of Macrophage-Like P33D1 Cells Stimulated by Arachidonic Acid*, Int J Neuropharmac 1987a; 9: 269–274.

Zavala et al., *Benzodiazepines and PK 11195 Expert Immunomodulating Activities by Binding on a Specific Receptor on Macrophages*, Ann NY Acad Sci 1987b; 496; 240–249.

Zisterer et al., *The Effects of the Peripheral-Type Benzodiazepine Acceptor Ligand, Ro 5-4864 and PK 11195, on mitochondrial Respiration*, Meth. Find. Clin. Pharmacol. 1992.

Klegeris et al., *Rat Brain Microglia and Peritoneal Macrophages Show Similar Responses to Respiratory Burst Stimulants*, J Neuroimmunology 1994; 53: 83–90.

Sprengel et al., *Molecular Cloning and Expression of cDNA Encoding a Peripheral-Type Benzodiazepine Receptor*, JBC 1989; 264(34): 20415–20421.

Parola et al. *Cloning and Expression of a Pharmacologically Unique Bovine Peripheral-type Benzodiazepine Receptor Isoquinoline Binding Protein*, JBC 1991; 266(21): 14082–14087.

Taketani et al., *Induction of Peripheral-type Benzodiazepine Receptors during Differentiation of Mouse Erythroleukemia Cells*, JBC 1994; 269(10): 7527–7531.

Toupin et al, Lymphokine & Cytokine Research, vol. 4 pp. 7–14 (1990).

PERIPHERAL BENZODIAZEPINE RECEPTOR LIGANDS AS ANTIINFLAMMATORY AGENTS

FIELD OF THE INVENTION

This invention pertains to the use of compounds which bind with high affinity to peripheral benzodiazepine receptors as antiinflammatory agents. Such compounds include isoquinoline and benzodiazepine derivatives. These compounds may be used in the treatment of human diseases such as rheumatoid arthritis, lupus erythematosus, Sjogren's syndrome, osteoarthritis, multiple sclerosis, Behcet's disease, temporal arteritis and dementia of the Alzheimer type.

BACKGROUND OF THE INVENTION

Historically, two broad classes of benzodiazepine receptors have been described: central and peripheral. Ligands for central benzodiazepine receptors, such as diazepam, flunitrazepam and clonazepam, produce an interaction with GABAA receptors, enhancing the activity of GABA (gamma-aminobutyric acid). These ligands possess anticonvulsant, muscle relaxant, sedative and anxiolytic properties. They are widely used clinically. The receptors are highly concentrated in brain, but are also found peripherally.

Ligands that are selective for peripheral benzodiazepine receptors, such as 4'-chlorodiazepam (Ro 5-4864) and 1-(2-chlorophenyl)-N-methyl-N-(1-methylpropyl)-3-isoquinolinecarboxamide (PK 11195), do not interact with GABA receptors and do not possess the same pharmacological properties as the central benzodiazepine receptor ligands. Instead they bind to peripheral benzodiazepine receptors which are widely distributed throughout the body, including the central nervous system. The peripheral benzodiazepine receptor ligands have no well defined pharmacological properties, and so far there are no generally accepted clinical applications for their use.

In this application, "peripheral benzodiazepine receptors" means the class of peripheral benzodiazepine receptors as distinguished from the class of central benzodiazepine receptors, and "peripheral benzodiazepine receptor ligands" means ligands that bind with high affinity to peripheral benzodiazepine receptors.

Of the known peripheral benzodiazepine receptor ligands, PK 11195 has the highest affinity. The equilibrium dissociation constant, or affinity (Kd) of PK 11195 for human brain tissue is estimated to be 4.3 nM (Doble et al., 1987). Its affinity for mouse peritoneal macrophages is reported to be 5.6 nM (Zavala and Lenfant, 1987b).

A compound's ability to displace bound PK 11195 from peripheral benzodiazepine receptors (Ki) is a convenient measure of the relative strength of the compound's binding to these receptors. In brain, this has been determined to be 3.5 nM for PK 11195 itself, 44 nM for 1-N,N-diethyl-a-methyl-2-phenylquinoline-4-propranamide (PK-14067), 178 nM for Ro 5-4864, and 46,000 nM for the central benzodiazepine receptor ligand clonazepam (Doble et al., 1987).

The peripheral benzodiazepine receptors are said to be highly associated, if not exclusively associated, with the outer mitochondrial membrane. The presumed association of these receptors with mitochondria (Snyder et al., 1990; Hirsch et al., 1989) has led to the proposal that they affect mitochondrial respiration. However, this view has been challenged on the basis of a poor correlation between receptor density and the ability of ligands to stimulate respiration (Zisterer et al., 1992).

The reported effects of peripheral benzodiazepine receptor ligands on immune function are diverse and in many respects contradictory. PK 11195 has been shown to inhibit in vitro mitogen-driven T- and B- cell stimulation, properties shared by a number of central benzodiazepine ligands (Ramseier et al., 1993; Bessler et al., 1992). In contrast, PK 11195 has also been reported to stimulate antibody production in mice following immunization with sheep red blood cells (Lenfant and Zavala, 1986; Zavala et al., 1984; Zavala and Lenfant, 1987b). Peripheral benzodiazepine receptor ligands, including Ro 5-4864, have also been reported to enhance the respiratory burst system of macrophage-like P388D1 cells stimulated with arachidonic acid. PK 11195 in the same situation reportedly had little effect (Zavala and Lenfant, 1987a).

In brain, peripheral benzodiazepine receptors are believed to be associated with glial cells. However, it is not clear what the physiological function of these receptors in brain might be. Various authors have reported increases in peripheral benzodiazepine receptor levels in rat brain following kainic acid, ischemic or neoplastic lesions. Similar findings have been reported for human brain tissue in patients with brain tumours, neoplasms, multiple sclerosis, cerebrovascular disorders and Alzheimer's disease. The teaching is that these increases in peripheral benzodiazepine receptor levels reflect glial proliferation (Diorio et al., 1991; Leong et al., 1994).

Following kainic acid lesioning to rat brain, binding of PK 11195 reportedly increased in both time and spatial localization with the appearance of macrophages, but PK 11195 binding apparently did not correlate with the appearance of astrocytes (Myers et al., 1991). In PET studies of human gliomas, there was a large increase in binding of PK 11195, but not of Ro 5-4684 (Junck et al., 1989).

It has been suggested that inhibitory agonists of peripheral benzodiazepine receptors are useful for speeding the recovery of damaged central nervous system tissue (Gee, 1993). The mechanisms proposed to account for this effect are inhibition of proliferation of glial cells and macrophages and inhibition of cytokine production by macrophages at the site of acute injury. But Taupin et al. (1991, 1993) find that the inflammatory cytokines interleukin-1 and tumor necrosis factor are increased, rather than decreased by peripheral benzodiazepine receptor ligands.

In summary, it can be said that the art and teaching in the field is inconsistent and has produced no overall concept as to the function of peripheral benzodiazepine receptors, or the pharmacological properties of their ligands.

SUMMARY OF THE INVENTION

The invention discloses that ligands which bind with high affinity to peripheral benzodiazepine receptors act as anti-inflammatory agents. A method of treating an inflammatory condition in a mammal is provided. The method comprises administering to a mammal requiring such treatment a therapeutically effective amount of a compound which binds with high affinity to peripheral benzodiazepine receptors. This may require dosages in the range of 0.01–10 mg/kilogram of body mass per day (0.03–32 micromoles/ kilogram per day), as determined by a medical practitioner or veterinarian. Preferably, the compound is selected from the group consisting of compounds which bind with submicromolar affinity to peripheral benzodiazepine receptors, PK 11195 for example, or pharmaceutically acceptable salts thereof.

The invention includes pharmaceutical compositions comprising a peripheral benzodiazepine receptor ligand in combination with one or more compatible pharmaceutically acceptable adjuvants or diluents which may be inert or physiologically active. These compositions may be administered by the oral, parenteral or rectal route or locally.

Compositions of the invention comprising a peripheral benzodiazepine ligand may be packaged in packaging material that comprises a label which indicates that the composition can be used for treating inflammatory conditions.

The present invention provides a method of identifying a compound that is therapeutically effective for treating an inflammatory condition in a mammal. The method comprises selecting a compound:

1) that binds with submicromolar affinity to peripheral benzodiazepine receptors; and,
2) that is therapeutically effective in treating inflammatory symptoms in MRL-lpr mice.

Additional steps may be taken in the method of identifying antiinflammatory compounds:

1) selecting the compound that inhibits respiratory burst in cultured macrophages; or,
2) selecting the compound that exhibits increased binding to human Alzheimer brain tissue compared to normal human brain tissue.

The compound utilized in the various aspects of the invention may be selected from the group consisting of: PK 11195, PK-14067, PK 14105, Ro5-6993, Ro5-4864, Ro5-6900, Ro5-6945, Ro5-6669, Ro5-6902, Ro5-6531, Ro5-3448, Diazepam, Ro7-5520, Ro5-5115, Ro5-4608, Ro5-6524, Ro5-5122. In each case, the compound is preferably 1-(2-chlorophenyl)-N-methyl-N-(1-methylpropyl)-3-isoquinolinecarboxamide (PK 11195).

DETAILED DESCRIPTION OF THE INVENTION

This invention discloses the use of high affinity peripheral benzodiazepine receptor ligands as a new class of antiinflammatory compounds. This class of compounds includes isoquinoline derivatives such as PK 11195 and benzodiazepine derivatives. The following examples illustrate various aspects of this invention, including three assays for defining the antiinflammatory pharmacological profile of such drugs. In the assays, the physiological effects of the powerful peripheral benzodiazepine receptor ligand PK 11195 have been evaluated in three standard paradigms. These assays establish the utility of high affinity benzodiazepine receptor ligands as antiinflammatory agents on the basis of the following results:

1) Pronounced therapeutic activity in the MRL-lpr mouse autoimmune disease. This disorder is an accepted model of a variety of human diseases: rheumatoid arthritis (Koopman and Gay, 1988) , systemic lupus erythematosus (Bartlett et al., 1988)., Sjogren's syndrome (Hayashi et al., 1994), connective tissue disease (Rosenberg, 1988), behavioral and neurological disorders (Sakic et al., 1993) and CNS inflammation (Vogelweid et al., 1991). PK 11195 demonstrated a more powerful prevention of pathology in this autoimmune disorder than standard antiinflammatory agents.
2) Down regulation of respiratory burst activity in cultured macrophages. PK 11195 was a more potent down regulator than standard antiinflammatory agents.
3) Enhanced high affinity binding to Alzheimer disease brain tissue compared with neurologically normal brain tissue. Cells involved in the inflammatory response in the central nervous system, including T-cells, reactive microglia (macrophages) and reactive astrocytes, (Itagaki, et al. 1986) are associated with Alzheimer disease lesions. Therefore, Alzheimer disease tissue is a model for inflammatory disease of the central nervous system. Both PK 11195 and Ro 5-4864 showed greater high affinity binding to Alzheimer brain tissue than to neurologically normal brain tissue, with the difference being greater for PK 11195.

Together, the foregoing assay results are predictive of the utility of PK 11195 and other peripheral benzodiazepine receptor ligands in the treatment of animal and human disorders of an inflammatory nature. These include, but are not limited to, rheumatoid arthritis, lupus erythematosus, Sjogren's syndrome, osteoarthritis, multiple sclerosis, inflammatory bowel disease, Behcet's disease, myasthenia gravis, temporal arteritis, Hashimoto's disease, dermatitis herpetiformis, and other diseases, including Alzheimer disease, where chronic inflammation may exacerbate the fundamental pathology (as discussed in more detail below).

EXAMPLE 1

Treating Inflammatory Conditions in MRL-lpr Mice

MRL-lpr mice are a widely studied strain which spontaneously develop a particularly severe autoimmune disorder. Pathologies that are found in a variety of human idiopathic inflammatory and autoimmune diseases are reproduced in these animals. They are therefore considered to be an outstanding model for such individual human diseases, although the pathology represents a combination of several of them. They are regarded as the best animal model for rheumatoid arthritis (Koopman and Gay, 1988) , systemic lupus erythematous (Bartlett et al., 1988)., and Sjogren's syndrome (Hayashi et al., 1994). They display vascular connective tissue disease (Rosenberg, 1988), as seen in several human arthropathies. They develop behavioral and neurological deficits (Sakic et al., 1993), as well as evidence of CNS inflammation (Vogelweid et al., 1991) which is seen in isolation in such diseases as Alzheimer type dementia and multiple sclerosis, but is also part of the syndrome in systemic lupus erythematosus and Sjogren's syndrome. The model is considered to be a particularly demanding one for screening antiinflammatory agents because of the severity and comprehensiveness of the disease pathology. The lesions are characterized by infiltration of b-lymphocytes and T-lymphocytes, indicating that it is a typical autoimmune disorder. The lesions include synovial inflammation, synovial cell proliferation, pannus formation, and articular cartilage erosion and bone destruction. Only powerful antiinflammatory agents will inhibit the devastating changes that accompany this genetic disorder. Mice of the MRL-lpr strain spontaneously develop a mild form of the disease at several months of age. The onset can be accelerated by injection of complete Freund's adjuvant (CFA) supplemented to 10 mg/ml with heat-inactivated M. tuberculosis, at 13–14 weeks of age, with 67–82% of animals becoming affected within 1 month (Ratkay et al., 1994 ; Ratkay et al., 1993).

Mice of the MRL-lpr strain were injected at 13–14 weeks of age with 0.05 ml of CFA supplemented to 10 mg/ml with heat-inactivated M. tuberculosis at each of two intradermal thoracic sites according to the standard procedure and, following injection (day 0), were started on a daily subcutaneous dose of PK 11195 dissolved in alcohol. Daily injections were continued until day 14. The animals were sacrificed at day 30 and joint histopathology assessed. Three dose levels of PK 11195 were employed: 0.1 mg/kg (N=10), 0.5 mg/kg (N=9), and 1 mg/kg (N=7). The results were compared with those in littermates receiving CFA only (N=7). Following sacrifice, animals were evaluated for subsynovial inflammation, synovial hyperplasia, cartilage destruction and pannus formation, and bone destruction. The results are shown in Table 1. PK 11195 reduced the total histopathological score observed in control mice by more than 70%, even at the lowest dose of 0.1 mg/kg. In comparison with results obtained by Ratkay et al., 1994, PK 11195, at the lowest dose, was more effective than ten times that dose of indomethacin, forty times that dose of cyclosporin, and whole body irradiation at 3 Gy from a 60cobalt source on day 1 of arthritis injection

TABLE 1

Inhibition of CFA-induced disease in MRL-1pr mice by PK 11195 (Mean ± S.D.) Severity of Disease Sign[A]

| Group | N | (1) | (2) | (3) | (4) | Total |
|---|---|---|---|---|---|---|
| Control | 7 | 2.14 ± 0.46 | 2.00 ± 0.38 | 0.71 ± 0.29 | 0.71 ± 0.36 | 5.57 ± 1.39 |
| PK 11195, 0.1 mg/kg | 10 | 0.70 ± 0.26 | 0.70 ± 0.26 | 0.00 ± 0.00 | 0.00 ± 0.00 | 1.40 ± 0.48 |
| PK 11195, 0.5 mg/kg | 8 | 0.62 ± 0.26 | 0.50 ± 0.27 | 0.00 ± 0.00 | 0.12 ± 0.12* | 1.25 ± 0.53 |
| PK 11195, 1 mg/kg | 7 | 0.43 ± 0.20 | 0.71 ± 0.18 | 0.00 ± 0.00 | 0.00 ± 0.00 | 1.14 ± 0.14 |

[A]The histopathological changes were assessed on a scale of 0 (no change) to 4 (severe change) for the following indices: (1) subsynovial inflammation; (2) synovial hyperplasia; (3) pannus formation; and (4) bone destruction. For methods see Ratkay et al., 1994.
*All PK 11195 data are significantly different from controls at $p < 0.001$ except this value for bone destruction which is significantly different from control at $p < 0.01$

EXAMPLE 2

Inhibiting Respiratory Burst in Cultured Macrophages

The respiratory burst system is an attack mechanism possessed by professional phagocytes such as peritoneal macrophages. Its main function is to protect the body from hostile invaders by generating superoxide radicals, but inappropriate activation can damage host tissue. Oxidative stress is believed to be one of the more harmful concomitants of inflammation. The respiratory burst system can be activated in cultured peritoneal macrophages in multiple ways, including exposure to zymosan particles opsonized by complement proteins (Klegeris and McGeer, 1994). The ability of PK 11195 to inhibit respiratory burst by administration before or after exposure of peritoneal macrophages to opsonized zymosan is shown in Table 2. At $10^{-4}$M, PK 11195 inhibited respiratory burst by more than 50% whether given before or after opsonized zymosan. This indicates that the effect was downstream from, or independent of, the opsonized zymosan receptors. Table 2 also shows the comparative effects of three agents effective in inflammatory disorders: indomethacin, prednisone and dapsone. Each of these agents was substantially less effective than PK 11195, and tended to show less inhibition when administered after opsonized zymosan than before. These data illustrate that PK 11195 inhibits respiratory burst activity more powerfully and by different mechanisms than these well known antiinflammatory agents. It is also more effective than 4'-chlorodiazepam, the prototype benzodiazepine ligand for peripheral benzodiazepine receptors.

TABLE 2

Inhibition of Respiratory Burst in Cultured Rat Peritoneal Macrophages by Various Substances

| Substance | Concentration | Percent of Control (± S.E.) when Substance was given | |
|---|---|---|---|
| | | Before OZ# | After OZ# |
| PK 11195 | $10^{-6}$M | 99.0 ± 5.6 | 97.9 ± 0.2 |
| | $10^{-5}$M | 87.9 ± 5.5 | 83.5 ± 8.7 |
| | $10^{-4}$M | 48.9 ± 10.8 | 47.1 ± 13.6 |
| Ro 5-4864 | $10^{-6}$M | 94.6 ± 12.2 | not done |
| | $10^{-5}$M | 85.4 ± 2.5 | not done |

TABLE 2-continued

Inhibition of Respiratory Burst in Cultured Rat Peritoneal Macrophages by Various Substances

| Substance | Concentration | Percent of Control (± S.E.) when Substance was given | |
|---|---|---|---|
| | | Before OZ# | After OZ# |
| | $10^{-4}$M | 74.7 ± 1.9 | not done |
| Indomethacin | $10^{-5}$M | 101.3 ± 3.5 | not done |
| | $10^{-4}$M | 86.3 ± 10.9 | 100.9 ± 2.1 |
| | $10^{-3}$M | 36 ± 12.5 | 64.8 ± 9.4 |
| Dapsone | $10^{-5}$M | 94.7 ± 1.3 | 96.4 ± 1.6 |
| | $10^{-4}$M | 73.6 ± 4.6 | 90.3 ± 6.2 |
| Prednisone | $10^{-4}$M | 88.8 ± 7.2 | 101.8 ± 4.9 |
| | $10^{-3}$M | 62.5 ± 8.1 | 67 ± 11.6 |

OZ# = opsonized zymosan.
For methods see Klegeris and McGeer, 1994.

EXAMPLE 3

Binding to Human Alzheimer Brain Tissue

To date, the only method by which the levels of putative peripheral benzodiazepine receptors in tissue can be determined is by high affinity binding of specific ligands such as PK 11195. To compare the levels in Alzheimer and normal brain tissue, we assessed the high affinity binding of PK 11195 to Alzheimer and normal brain tissue. The standard method of Schoemaker et al., 1983 was employed.

TABLE 3

Specific High Affinity Binding of PK 11195 (at 3 nM) to Alzheimer and Control Cortical Tissue (in fentamoles/mg protein)

| Alzheimer | Control |
|---|---|
| 480 | 201 |
| 585 | 94 |
| 400 | 265 |
| 450 | 118 |
| 395 | 141 |
| 408 | 111 |

TABLE 3-continued

Specific High Affinity Binding of PK 11195
(at 3 nM) to Alzheimer and Control Cortical Tissue
(in fentamoles/mg protein)

|  | Alzheimer | Control |
| --- | --- | --- |
| Means ± S.E. | 422<br>449 ± 25 | 222<br>165 ± 25 |

(difference significant at p < 0.001)

The results are shown in Table 3 for Alzheimer and control brain tissue. As shown in the table, Alzheimer cases had 2.7 fold higher binding of PK 11195 than control brain tissue. This is greater than the difference observed with Ro 5-4864 (McGeer et al., 1988).

A criterion by which the potency of other isoquinoline or benzodiazepine derivatives can be compared with PK 11195 is their ability to displace PK 11195 in a competitive binding assay (Doble et al., 1987).

EXAMPLE 4

A Method of Identifying Novel Antiinflammatory Compounds

The invention provides a method of identifying a compound that is therapeutically effective for treating an inflammatory condition in a mammal. The method comprises selecting a compound:

1) that binds with submicromolar affinity to peripheral benzodiazepine receptors; and,
2) that is therapeutically effective in treating inflammatory symptoms in MRL-lpr mice.

Additional steps may be taken in the method of identifying antiinflammatory compounds:

1) selecting the compound that inhibits respiratory burst in cultured macrophages; or,
2) selecting the compound that exhibits increased binding to human Alzheimer brain tissue compared to normal human brain tissue.

In the method of identifying antiinflammatory compounds, the compound may be selected from the group consisting of: PK 11195, PK-14067, PK 14105, Ro5-6993, Ro5-4864, Ro5-6900, Ro5-6945, Ro5-6669, Ro5-6902, Ro5-6531, Ro5-3448, Diazepam, Ro7-5520, Ro5-5115, Ro5-4608, Ro5-6524, Ro5-5122, therapeutically acceptable salts of these compounds or mixtures of these compounds or their salts.

EXAMPLE 5

Methods of Treatment

A method of treating an inflammatory condition in a mammal is provided. The method comprises administering to a mammal requiring such treatment a therapeutically effective amount of a compound, or a pharmaceutically acceptable salt of the compound, the compound being selected from the group consisting of compounds which bind with submicromolar affinity to peripheral benzodiazepine receptors. The method may be practised where the mammal is a human being and the compound binds with submicromolar affinity to human peripheral benzodiazepine receptors. The inflammatory condition may be rheumatoid arthritis, lupus erythematosus, Sjogren's syndrome, osteoarthritis, multiple sclerosis, Behcet's disease, temporal arteritis, and, without being limited by the foregoing, any inflammatory disorder which calls for the use of antiinflammatory agents. Alternatively, the inflammatory condition may be dementia of the Alzheimer type and the peripheral benzodiazepine receptors may be those that are found in brain. Dementia of the Alzheimer type is included in this catagory since it has been shown to be characterized by chronic inflammation of the brain and to respond to antiinflammatory therapy (U.S. Pat. No. 5,192,753).

A preferred compound is PK 11195. However, the compound may be selected from the group consisting of: PK 11195, PK-14067, PK 14105, Ro5-6993, Ro5-4864, Ro5-6900, Ro5-6945, Ro5-6669, Ro5-6902, Ro5-6531, Ro5-3448, Diazepam, Ro7-5520, Ro5-5115, Ro5-4608, Ro5-6524, Ro5-5122, therapeutically acceptable salts of these compounds or mixtures of these compounds or their salts.

EXAMPLE 6

Formulations

The invention includes pharmaceutical compositions comprising a peripheral benzodiazepine receptor ligand in combination with one or more compatible pharmaceutically acceptable adjuvants or diluents which may be inert or physiologically active. These compositions may be administered by the oral, parenteral or rectal route or locally. The peripheral benzodiazepine receptor ligand may be PK 11195. However, the ligand may be selected from the group consisting of: PK 11195, PK-14067, PK 14105, Ro5-6993, Ro5-4864, Ro5-6900, Ro5-6945, Ro5-6669, Ro5-6902, Ro5-6531, Ro5-3448, Diazepam, Ro7-5520, Ro5-5115, Ro5-4608, Ro5-6524, Ro5-5122,therapeutically acceptable salts of these compounds or mixtures of these compounds or their salts.

Tablets, pills, powders (gelatin capsules or cachets) or granules, may be used as solid compositions for oral administration. In these compositions, the active ingredient according to the invention may be mixed with one or more inert diluents such as starch, cellulose, sucrose, lactose or silica. These compositions may also contain substances other than diluents, for example one or more lubricants such as magnesium stearate or talcum, a colorant, a coating (dragees) or a lacquer.

Pharmaceutically acceptable solutions, suspensions, emulsions, syrups and elixirs containing inert diluents such as water, ethanol, glycerol, benzoic acid, benzyl alcohol, sodium benzoate, dimethyl sulfoxide, vegetable oils or liquid paraffin may be used as liquid compositions for oral administration. These compositions may contain substances other than diluents, for example wetting agents, sweeteners, thickeners, flavoring agents or stabilizers.

Sterile compositions for parenteral administration may preferably be non-aqueous solutions, suspensions or emulsions. Water, propylene glycol, polyethylene glycol, benzoic acid, benzyl alcohol, sodium benzoate, dimethyl sulfoxide, vegetable oils, especially olive oil, injectable organic acids esters, for example ethyl oleate or other suitable organic solvents may be used as the solvent or the carrier.

These compositions may also contain adjuvants, especially wetting agents, tonicity regulating agents, emulsifiers, dispersants and stabilizers. The sterilization may be carried out in several ways, for example by aseptic filtration, incorporating a sterilizing agent, by irradiation or by heating. They may also be prepared in the form of sterile solid compositions which may be dissolved at the time of use in a sterile medium suitable for injection.

Compositions for rectal administration are suppositories or rectal capsules, which contain, in addition to the active product, excipients such as cocoa butter, semi-synthetic glycerides or polyethylene glycols.

Compositions for local administration may be for example creams, ointments, lotions, eye lotions, mouthwashes, nasal drops or aerosols.

The dosage depends on the effect sought, the length of treatment and the administration route employed. In general, the medical practitioner (or veterinarian) will determine the appropriate dosage depending on the age, weight and all other factors specific to the subject to be treated. The approximate dosage range may be chosen from the dosage range shown to be effective in resisting damage in the MRL-lpr murine rheumatoid arthritis model, i.e. 0.01 mg/kg to 10 mg/kg, with the most probable range being 0.1–1 mg/kg body weight per day.

EXAMPLE 7

Articles of Manufacture

Compositions of the invention comprising a peripheral benzodiazepine ligand may be packaged in packaging material that comprises a label which indicates that the composition can be used for treating inflammatory conditions. Such conditions include rheumatoid arthritis, lupus erythematosus, Sjogren's syndrome, osteoarthritis, multiple sclerosis, Behcet's disease, temporal arteritis, dementia of the Alzheimer type. The peripheral benzodiazepine ligand of the composition preferably exhibits submicromolar affinity to peripheral benzodiazepine receptors, for example PK 11195. The ligand may be selected from the group consisting of: PK 11195, PK-14067, PK 14105, Ro5-6993, Ro5-4864, Ro5-6900, Ro5-6945, Ro5-6669, Ro5-6902, Ro5-6531, Ro5-3448, Diazepam, Ro7-5520, Ro5-5115, Ro5-4608, Ro5-6524, Ro5-5122, therapeutically acceptable salts these compounds or mixtures of these compounds or their salts.

References

The following publications are incorporated herein by reference:

Bartlett, R. R., Popovic, S., Raiss, R. X., *Development of autoimmunity in MRL/lpr mice and the effects of drugs on this murine disease*, Scand J Rheumatol—Suppl 1988; 75:290-299.

Bessler, H., Weizman, R., Gavish, M., Notti, I., Djaldetti, M. *Immunomodulatory effect of peripheral benzodiazepine receptor ligands on human mononuclear cells*. J Neuroimmunol 1992; 38: 19–26.

Diorio, D., Welner, S. A., Butterworth, R. F., Meaney, M. J., Suranyi-Cadotte, B. E. *Peripheral benzodiazepine binding sites in Alzheimer's disease frontal and temporal cortex.* Neurobiol Aging 1991; 12: 255–258;

Doble, A., Malgouris, C., Daniel, M., Daniel, N., Imbault, F., Basbaum, A., Uzan, A., Gueremy, C., and Le Fur, G. *Labelling of peripheral-type benzodiazepine binding sites in human brain with [3H]PK 11195: anatomical and subcellular distribution.* Brain Res Bull 1987; 18: 49–61.

Gee, K. W. *Use of Peripheral-Type Benzodiazepine Sites for Treatment of CNS Trauma or Disease.* International Patent Application No. PCT/US92/10729, International Publication Number WO 93/1177, 1993.

Hayashi, Y., Haneji, N., Hamano, H. *Pathogenesis of Sjogren's syndrome-like autoimmune lesions in MRL/lpr mice*[Review], Pathol Int 1994; 44:559–568.

Hirsch, J. D., Beyer, C. F., Malkowitz, L., Loullis, C. C., Blume, A. J. *Characterization of ligand binding to mitochondrial benzodiazepine receptors.* Mol Pharmacol 1989; 35: 164–172.

Itagaki, S., McGeer, P. L. and Akiyama, H., Presence of cytotoxic suppressor and leucocyte common antigen positive cells in Alzheimer's disease brain tissue. Neurosci. Lett., 91 (1988) 259–264.

Junck, L., Olson, J. M., Ciliax, B. J. et al. *PET imaging of human gliomas with ligands for the peripheral benzodiazepine binding site.* Ann Neurol 1989; 26:752–758.

Klegeris, A., McGeer, P. L. *Inhibition of respiratory burst in macrophages by complement receptor blockade.* Eur J Pharmacol 1994; 260: 273–277.

Koopman, W. J., Gay, S. *The MRL-lpr mouse. A model for the study of rheumatoid arthritis* [Review]. Scand J Rheumatol—Suppl 1988; 75:284–289.

Lenfant, M. and Zavala, F. *In vivo immunomodulating activity of PK 11195, a structurally unrelated ligand for peripheral benzodiazepine binding sites. I. Potentiation in mice of the humoral response to sheep red blood cells.* Int. J. Immunopharmacol 1986; 8, 825–828.

Leong, D. K., Le, O., Oliva, L., Butterworth, R. F. *Increased densities of binding sites for the "peripheral-type" benzodiazepine receptor ligand [3H]PK11195 in vulnerable regions of the rat brain in thiamine deficient encephalopathy.* J Cereb Blood Flow Metab 1994; 14: 100–105.

McGeer, E. G., Singh, E. A., McGeer, P. L. *Peripheral-type benzodiazepine binding in Alzheimer disease.* Alz Dis Assoc Disorders 1988; 2: 331–336.

McGeer, P. L., Rogers, J., McGeer, E. G., Sibley, J. *Anti-rheumatoid arthritic drugs in the treatment of dementia.* U.S. Pat. No. 5,192,753 issued 9 Mar. 1993.

Myers, R., Manjil, L. G., Cullen, B. M., Price, G. W., Frackowiak, R. S. J., Cremer, J. E. *Macrophage and astrocyte populations in relation to [3H]PK 11195 binding in rat cerebral cortex following a local ischaemic lesion.* J Cerebral Blood Flow Metab 1991; 11: 314–322.

Ramseier, H., Lichtensteiger, W., Schlumpf, M. *In vitro inhibition of cellular immune responses by benzodiazepines and PK 11195.* Immunopharmacol Immunotoxicol 1993; 15: 557–582.

Ratkay, L. G., Chowdhary, R. K., Neyndorff, H. C., Tonzetich, J., Waterfield, J. D., Levy, J. G. *Photodynamic therapy: a comparison with other immunomodulatory treatments of adjuvant-enhanced arthritis in MRL-lpr mice.* Clin Exp Immunol 1994; 95: 373–377.

Ratkay, L. G., Zhang, L., Tonzetich, J., Waterfielf, J. D. *Complete Freund's adjuvant induces an earlier and more severe arthritis in MRL-lpr mice.* J Immunol 1993; 151:5081–5087.

Rosenberg, N. L. *Neuromuscular histopathology in (New Zealand black×New Zealand white)F1 and MRL-lpr autoimmune mice: models for skeletal muscle involvement in connective tissue disease.* Arthritis Rheumatism 1988; 31: 806–811.

Sakic, B., Szechtman, H., Denburg, S., Carbotte, R., Denburg, J.A. *Brain-reactive antibodies and behavior of autoimmune MRL-lpr mice.* Physiol Behavior 1993; 54:1025–1029.

Schoemaker, H., Boles, R. G., Horst, D., Yamamura, H. I. *Specific high affinity binding sites for [3H]Ro 5-4864 in rat brain and kidney.* J Pharm Exp Ther 1983; 225:61–69.

Snyder, S. H., McEnery, M. W., Verma, A. *Molecular mechanism of peripheral benzodiazepine receptors.* Neurochem Res 1990; 15: 119–123.

Taupin, V., Herbelin, A., Descamps-Latscha, B. and Zavala, F., Endogenous anxiogenic peptide, ODN-diazepam binding inhibitor, and benzodiazepines enhance the production of interleukin-1 *and tumor necrosis factor by human monocytes.* Lymphokine & Cytokine Res., 10 (1991) 7–13 and Taupin, V.; Toulmond, S.; Serrano, A.; Benavides, J. and Zavala, F. *Increase in IL-6, IL-1* and TNF levels in rat brain following traumatic lesions. J. Neuroimmunol; 42 91993 177–186.

Vogelweid, C. M., Johnson, G. C., Besch-Williford, C. L., Basler, J., Walker, S. E. *Inflammatory central nervous system disease in lupus-prone MRL/lpr mice: comparative histologic and immunohistochemical findings.* J Neuroimmunol 1991; 35:89–99.

Zavala, F., Haumont, J., Lenfant, M. *Interaction of benzodiazepines with mouse macrophages.* Eur J Pharmac 1984; 106:561–566.

Zavala, F., Lenfant, M. *Peripheral benzodiazepines enhance the respiratory burst of macrophage-like P33D1 cells stimulated by arachidonic acid.* Int J Neuropharmac 1987a; 9:269–274.

Zavala, F., Lenfant, M. *Benzodiazepines and PK 11195 exert immunomodulating activities by binding on a specific receptor on macrophages.* Ann NY Acad Sci 1987b; 496:240–249.

Zisterer, D. M., Gorman, A. M. C., Williams, C., Murphy, M. P. *The effects of the peripheral-type benzodiazepine acceptor ligands, Ro 5–4864 and PK 11195, on mitochondrial respiration.* Meth. Find. Exp. Clin. Pharmacol. 1992; 14: 85–90.

As will be apparent to those skilled in the art of the invention in the light of the foregoing disclosure, many alterations and modifications are possible in the practice of this invention without departing from the spirit and scope thereof. Accordingly, the scope of the invention is to be construed in accordance with the substance defined by the claims.

What is claimed is:

1. A method of alleviating a chronic inflammatory condition in a mammal, which comprises administering to a mammal suffering from a chronic inflammatory condition, a compound, or a pharmaceutically acceptable salt of the compound, selected from the group consisting of compounds which bind with submicromolar affinity to peripheral benzodiazepine receptors in mammalian tissue, said compound, or a pharmaceutically acceptable salt of the compound, being administered to said mammal at a dosage in the range of 0.01–10 mg/kilogram of body mass per day.

2. The method of claim 1 wherein the mammal is a human being and the compound binds with submicromolar affinity to human peripheral benzodiazepine receptors.

3. The method of claim 2, wherein the inflammatory condition is dementia of the Alzheimer type and the peripheral benzodiazepine receptors are found in brain.

4. The method of claim 2, wherein the inflammatory condition is rheumatoid arthritis.

5. The method of claim 2, wherein the inflammatory condition is lupus erythematosus.

6. The method of claim 2 where the inflammatory condition is Sjogren's syndrome.

7. The method of claim 1 wherein the compound is 1-(2-chlorophenyl)-N-methyl-N-(1-methylpropyl)-3-isoquinolinecarboxamide.

8. The method of claim 2 wherein the compound is 1-(2-chlorophenyl)-N-methyl-N-(1-methylpropyl)-3-isoquinolinecarboxamide.

9. The method of claim 3 wherein the compound is 1-(2-chlorophenyl)-N-methyl-N-(1-methylpropyl)-3-isoquinolinecarboxamide.

10. The method of claim 4 wherein the compound is 1-(2-chlorophenyl)-N-methyl-N-(1-methylpropyl)-3-isoquinolinecarboxamide.

11. The method of claim 5 wherein the compound is 1-(2-chlorophenyl)-N-methyl-N-(1-methylpropyl)-3-isoquinolinecarboxamide.

12. The method of claim 6 wherein the compound is 1-(2-chlorophenyl)-N-methyl-N-(1-methylpropyl)-3-isoquinolinecarboxamide.

13. The method of claim 1 wherein the compound is selected from the group consisting of: PK 11195, PK 14067, PK 14105, Ro5–6993, Ro5–4864, Ro5–6900, Ro5–6945, Ro5–6669, Ro5–6902, Ro5–6531, Ro5–3448, Diazepam, Ro7-5520, Ro5–5115, Ro5–4608, Ro5–6524, Ro5–5122, therapeutically acceptable salts of these compounds or mixtures of these compounds or their salts.

14. The method of claim 1 wherein the compound, or a pharmaceutically acceptable salt of the compound, is administered to the mammal orally, parenterally, rectally or locally.

* * * * *